US008005534B2

(12) United States Patent
Greenwald et al.

(10) Patent No.: US 8,005,534 B2
(45) Date of Patent: Aug. 23, 2011

(54) SYSTEM AND METHOD FOR PREDICTION OF ADVERSE EVENTS DURING TREATMENT OF PSYCHOLOGICAL AND NEUROLOGICAL DISORDERS

(75) Inventors: Scott D. Greenwald, Brookline, MA (US); Philip H. Devlin, Brookline, MA (US); Jeffrey C. Sigl, Medway, MA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 719 days.

(21) Appl. No.: 11/330,593

(22) Filed: Jan. 12, 2006

(65) Prior Publication Data

US 2006/0167370 A1    Jul. 27, 2006

Related U.S. Application Data

(60) Provisional application No. 60/643,350, filed on Jan. 12, 2005.

(51) Int. Cl.
*A61B 5/04*    (2006.01)
(52) U.S. Cl. ...................................................... 600/544
(58) Field of Classification Search .......... 600/544–545, 600/345, 347, 365; 607/45, 48
See application file for complete search history.

(56) References Cited

U.S. PATENT DOCUMENTS

| | | | |
|---|---|---|---|
| 4,407,299 A * | 10/1983 | Culver | 600/544 |
| 4,533,346 A | 8/1985 | Cosgrove, Jr. et al. | |
| 4,736,751 A | 4/1988 | Gevins et al. | |
| 4,862,359 A | 8/1989 | Trivedi et al. | |
| 4,907,597 A | 3/1990 | Chamoun | |
| 5,010,891 A | 4/1991 | Chamoun | |
| 5,083,571 A * | 1/1992 | Prichep | 600/544 |
| 5,119,816 A | 6/1992 | Gevins | |
| 5,230,346 A | 7/1993 | Leuchter et al. | |
| 5,269,315 A | 12/1993 | Leuchter et al. | |
| 5,299,569 A | 4/1994 | Wernicke et al. | |
| 5,309,923 A | 5/1994 | Leuchter et al. | |
| 5,311,876 A | 5/1994 | Olsen et al. | |
| 5,320,109 A | 6/1994 | Chamoun et al. | |
| 5,331,970 A | 7/1994 | Gevins et al. | |
| 5,458,117 A | 10/1995 | Chamoun et al. | |
| 5,568,816 A | 10/1996 | Gevins et al. | |
| 5,846,208 A | 12/1998 | Pichlmayr et al. | |

(Continued)

FOREIGN PATENT DOCUMENTS

WO    WO 03/057029    7/2003

(Continued)

OTHER PUBLICATIONS

Brent, David et al., "Early-Onset Mood Disorder", www.acnp.org/g4/GN40100158/CH154.html, printed Nov. 10, 2008.

(Continued)

*Primary Examiner* — Patricia C Mallari

(57) ABSTRACT

The present invention is a system and method of deriving and computing features and indices that predict the likelihood of psychological and neurological adverse events such as suicidal thoughts and/or actions. The method of the present invention further predicts the likelihood of suicidal thoughts and/or actions prior to and or during treatment for psychological disease. To obtain such features and indices, power spectrum and time domain values are derived from biopotential signals acquired from the subject being tested. The system and method identify people who are likely to experience changing, especially worsening, symptoms of psychological and neurological adverse events such as suicidal thoughts or actions and who therefore may be at risk (e.g. suicide).

10 Claims, 6 Drawing Sheets

U.S. PATENT DOCUMENTS

| | | | |
|---|---|---|---|
| 5,871,517 A | 2/1999 | Abrams et al. | |
| 6,024,707 A * | 2/2000 | Scinto et al. | 600/558 |
| 6,066,163 A | 5/2000 | John | |
| 6,205,359 B1 | 3/2001 | Boveja | |
| 6,263,237 B1 | 7/2001 | Rise | |
| 6,304,775 B1 | 10/2001 | Lasemidis et al. | |
| 6,343,229 B1 | 1/2002 | Siebler et al. | |
| 6,425,852 B1 | 7/2002 | Epstein et al. | |
| 6,459,936 B2 | 10/2002 | Fischell et al. | |
| 6,463,328 B1 | 10/2002 | John | |
| 6,539,263 B1 | 3/2003 | Schiff et al. | |
| 6,622,036 B1 * | 9/2003 | Suffin | 600/544 |
| 7,206,632 B2 * | 4/2007 | King | 600/544 |
| 7,231,245 B2 | 6/2007 | Greenwald et al. | |
| 2002/0012312 A1 | 1/2002 | Ogasawara et al. | |
| 2002/0013612 A1 | 1/2002 | Whitehurst | |
| 2002/0013812 A1 | 1/2002 | Krueger et al. | |
| 2003/0023282 A1 | 1/2003 | Barrett et al. | |
| 2003/0135128 A1 * | 7/2003 | Suffin et al. | 600/544 |
| 2003/0181821 A1 | 9/2003 | Greenwald et al. | |
| 2003/0204135 A1 | 10/2003 | Bystritsky | |
| 2005/0043774 A1 * | 2/2005 | Devlin et al. | 607/45 |
| 2005/0216071 A1 * | 9/2005 | Devlin et al. | 607/48 |

FOREIGN PATENT DOCUMENTS

| | | |
|---|---|---|
| WO | WO 2004/100765 | 11/2004 |

OTHER PUBLICATIONS

Diego, Miguel A. et al., "CES-D Depression Scores Are Correlated With Frontal EEG Alpha Asymmetry", Depression and Anxiety 13:32-37 (2001).

Graae, Flemming et al., "Abnormality of EEG Alpha Asymmetry in Female Adolescent Suicide Attempters", Biol. Physchiatry 40:706-713 (1996).

Hunter, Aimee M. et al. "Neurophysiologic Correlates of Side Effects in Normal Subjects Randomized to Venlafaxine or Placebo", Neurophysopharmacology 1-8 (2004).

Struve, Frederick A., "Electroencephalographic Relationship to Suicidal Behavior: Qualitative Considerations and a Report on a Series of Completed Suicides", Clin. Electroencephalography, vol. 14 (1): 20-26 (1983).

Struve, Frederick A., "Possible Potentiation of Suicide Risk in Patients with EEG Dysrhythmias Taking Oral Contraceptives: A Speculative Empirical Note", Clin. Electroencephalography, vol. 16 (2): 88-90 (1985).

Struve, Frederick A., Suide and Life-Threatening Behavior, vol. 16(2), Ch. 3 "Clinical Electroencephalography and a Study of Suicide Behavior", pp. 51-83 (Summer 1986).

Alkire, Michael T., Quantitative EEG Correlations with brain Glucose Metabolic Rate during Anesthesia in Volunteers, Anesthesiology, 98:323-33 (1998).

Besthorn et al., "Discrimination of Alzheimer's Disease and Normal Aging by EEG Data," Electroencephalography and Clin. Neurophysiology, 103:241-48 (1997).

Coben et al., "A Longitudinal EEG Study of Mild Senile Dementia of Alzheimer Type: Changes at 1 Year and at 2.5 Years," Electroencephalogr. Clin. Neurophysiol., 2:101-12 (1985).

Claus et al., "The Diagnostic Value of Electroencephalography in Mild Senile Alzheimer's Disease," Clin. Neurophysiology, 110:825-32 (1999).

Cook et al., "Prefrontal Changes and Treatment Response Prediction in Depression," Seminar in Clinical Neuropsychiatry, 6:113-20 (2001).

Diego et al., "CES-D Depression Scores are Correlated with Frontal EEG Alpha Asymmetry," Depression and Anxiety, 13:32-7 (2001).

Folstein, et al., "Mini-Mental State a Practical Method for Grading the Cognitive State of Patients for the Clinician," J. Psychiat res., 12:189-98 (1975).

Glass et al., "Bispectral Analysis Measures Sedation and Memory Effects of Propofol, Midazolam, Isoflurane, and Alfentanil in Health Volunteers," Anesthesiology, 86:836-47 (1997).

Hamilton, M., "A Rating Scale for Depression," J. Neurol. Neurosurg. Psychiat., 23:56-62 (1960).

Hassainia et al., "Quantitative EEG and Statistical Mapping of Wakefulness and REM Sleep in the Evaluation of Mild to Moderate Alzheimer's Disease," Eur. Neurol., 37:219-24 (1997).

Holschneider et al., "Loss of High-Frequency Brain Electrical Response to Thipental Administration in Alzheimer's-Type Dementia," Neurophycopharmacology, 16:26-275 (1997).

Jonkman, EJ., "The Role of the Electroencephalogram in the Diagnosis of Dementia of the Alzheimer Type: an Attempt at Technology Assessment," Neurophysiol. Clin. 27:211-19 (1997).

Knott, Verner 1., "Quantitative EEG in the Prediction of Antidepressant Response to Imipramine," J. Affective Disorders, 39: 175-84 (1996).

Knott et al., "Pre-Treatment EEG and Its Relationship to Depression Severity and Paroxetine Treatment Outcome," Pharmacopsychiatry, 33:302-05 (2000).

Leuchter, A. F., "Regional Differences in Brain Electrical Activity in Dementia: Use of Spectral Power and Spectral Ratio Measures," Electroencephalography and Clinical Neurophysiology, 87:385-93 (1993).

McKhann et al., "Clinical Diagnosis of Alzheimer's Disease: Report of the NINCDS-ADRDA Work Group Under the Auspices of Department of Health and Human Services Task Force on Alzheimer's Disease," Neurology, 34:939-44 (1984).

Neufeld, M.Y., "Effects of a Single Intravenous Dose of Scopolamine on the Quantitative EEG in Alzheimer's Disease Patients and Age-Matched Controls," Electroencephalography and Clin. Neurophysiology, 91:407-12 (1994).

Pezard, L., "Entropy Maps Characterizer Drug Effects on Brain Dynamics in Alzheimer's Disease," Neuroscience Letters, 253:5-8, (1998).

Rampil, I., "A Primer for EEG Signal Processing in Anesthesia," Anesthesiology, 89(4):980-1002 (1998).

Renna, M., "Does Dementia Affect the Bispectral Index?" Amer. Society of Anesthesiologists, p. 1 of 2 (2001).

Jasper, H. H., "The Ten-Twenty Electrode System of the International Federation in Electroencephalography and Clinical Neurology,"• The EEG Journal, 10 (Appendix):371-75 (1958).

Murphy et al., •Stimulation of the Nervous System for the Management of Seizures: CNS Drugs. 17(2):101-15 (2003).

Marqui et al., International Journal of Psychophysiology, 18:49-65 (1994).

Pizzagalli. et al., "Anterior Cingulate Activity as a Predictor of Degree of Treatment Response in Major Depression: Evidence from Brain Electrical Tomography Analysis", American Journal of Psychiatry, 158:3, 405-15 (2001).

Struys, M.D., Michel, RUGLOOP Software, Univ. of Gent, department of Anaesthesia, Belgium (1995).

* cited by examiner

SYSTEM AND METHOD FOR PREDICTION OF ADVERSE EVENTS DURING TREATMENT OF PSYCHOLOGICAL AND NEUROLOGICAL DISORDERS

CROSS REFERENCE TO RELATED APPLICATION

This application claims benefit of U.S. Provisional Application Ser. No. 60/643,350 filed on Jan. 12, 2005.

BACKGROUND

Depression is a mood disorder that affects 17 million Americans each year, and is responsible for 9.7 million doctor visits. It affects sufferers in a variety of ways, resulting in depressed mood, irritability, sleep disorders, feelings of agitation, guilt and worthlessness, loss of energy and initiative, an inability to concentrate and an increased incidence of suicide. There are a number of antidepressant pharmacological agents, and once the proper treatment is determined, their effectiveness is quite high.

Major Depressive Disorder (MDD) is the psychiatric diagnosis most commonly associated with completed suicide. The American Association of Suicidology notes on their website that the lifetime risk of suicide among patients with untreated MDD is nearly 20%. About ⅔ of people who complete suicide are depressed at the time of their deaths. In a study conducted in Finland, of 71 individuals who completed suicide and who had Major Depressive Disorder, only 45% were receiving treatment at the time of death and only a third of these were taking antidepressants.

Evidence suggests that pharmacological treatment of some depressed subjects may increase the risk of suicidal thinking and behavior in adolescents. Development of methods to identify those subjects who are at increased risk of developing adverse events, especially suicide, would provide significant benefit to both patients and clinicians.

Cook et al. demonstrated that pre-frontal electroencephalographic (EEG) cordance, a quantitative EEG (QEEG) parameter, predicts successful response to fluoxetine antidepressant therapy. Greenwald et al. in U.S. patent application Ser. No. 10/337,088 described the use of EEG indices using bispectral features to assess the severity of depression and to predict response to antidepressant pharmacological treatment. It has been reported that side effect burden, characterized as the mean number of side effects per clinical visit, correlated with changes in an EEG index (prefrontal cordance) during the placebo lead-in period in patients receiving antidepressant treatment, but not in a placebo control group.

Others have observed that abnormal electroencephalographic (EEG) activity has been associated with various psychiatric disorders and behaviors, including depression, suicide, and aggression and reported that differences in the intrahemispheric distribution of EEG alpha band power (alpha asymmetry), particularly over posterior regions of the scalp, differed between adolescent female suicide attempters and matched controls. Specifically, the controls exhibited greater EEG alpha band power over right than left hemispheres as compared to suicide attempters. Note that this study was not a prediction of the risk of suicidal behavior, but an observational study of EEG patterns conducted subsequent to suicide attempts. Several researchers have reported that paroxysmal EEG abnormalities increase the risk of suicide in patients.

SUMMARY OF THE INVENTION

The present invention is a system and method of deriving and computing features and indices that predict the likelihood of psychological and neurological adverse events such as suicidal thoughts and/or actions. The method of the present invention further predicts the likelihood of suicidal thoughts and/or actions prior to and or during treatment for psychological disease. To obtain such features and indices, power spectrum and time domain values are derived from biopotential signals acquired from the subject being tested. The system and method identify people who are likely to experience changing, especially worsening, symptoms of psychological and neurological adverse events such as suicidal thoughts or actions and who therefore may be at risk (e.g. suicide).

DETAILED DESCRIPTION OF THE PREFERRED EMBODIMENTS

Figure 1:
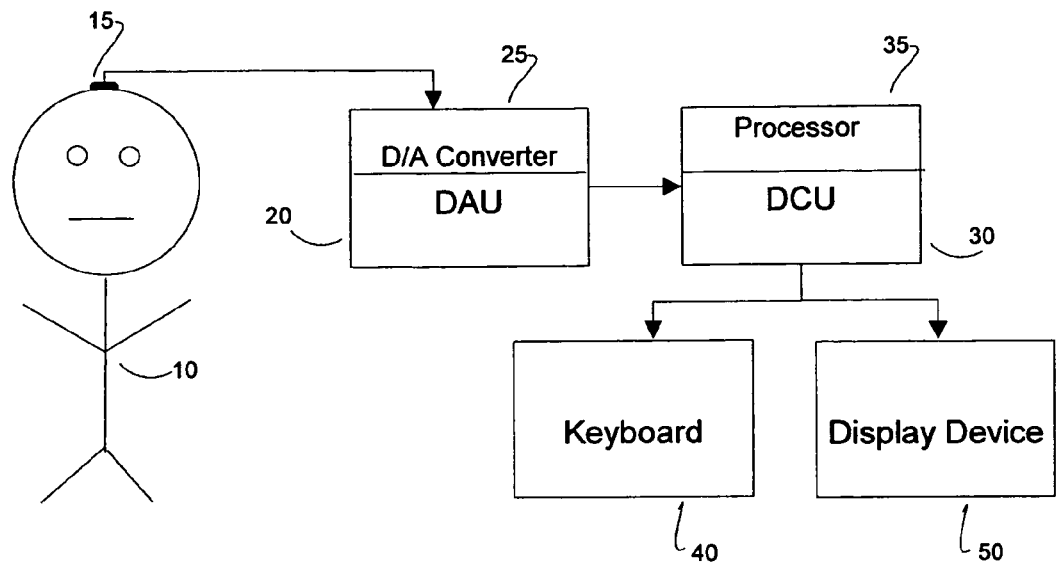
FIG. 1 is a block diagram of the system of the present invention for predicting adverse events during treatment of psychological and neurological disorders.
Figure 2:
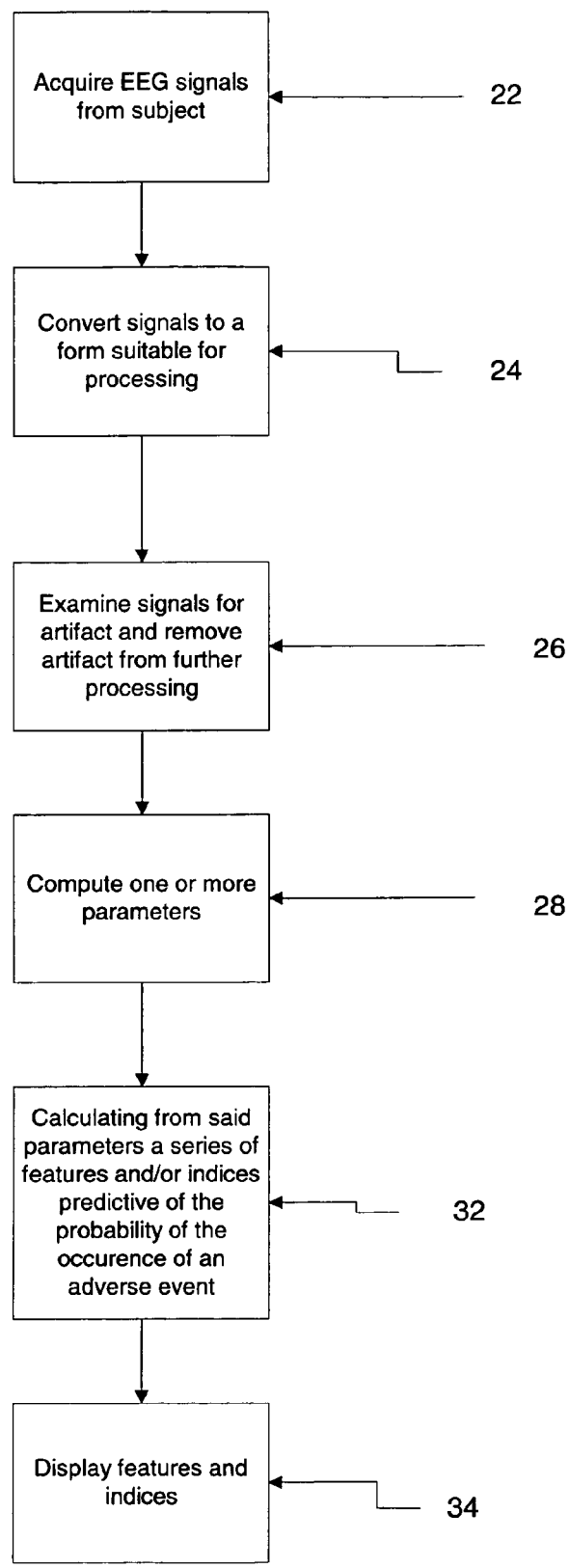
FIG. 2 is a flow chart of the steps of the method of the present invention.

Referring to FIGS. 1 and 2, a preferred embodiment of the present invention shown in FIG. 1 incorporates a Data Acquisition Unit (DAU) 20 that is used to acquire an EEG signal in step 22 from a subject 10 for subsequent processing. The DAU 20 typically consists of a computer system with an integral analog-to-digital (A-D) converter 25 and a set of electrodes that is representatively shown placed on the scalp of a subject 10. While only a single electrode 15 is shown, any montage of electrodes used to obtain EEG signals may be used in the invention. The A-D converter 25 is used to transform in step 24 the analog EEG signals obtained from the electrodes 15 into a sampled set of signal values that may then be analyzed by the processor 35 of a Data Computation Unit (DCU) 30. The DCU 30 incorporates a processor 35 and a communications device that receives the sampled values from the DAU 20. In the preferred embodiment, the processors of the DAU 20 and DCU 30 are one and the same. In an alternate embodiment, however, the DAU 20 may acquire the EEG signals and transmit the sampled EEG signals over a communications link to a remote DCU 30. Such a communications link may be a serial or parallel data line, a local or wide area network, a telephone line, the Internet, or a wireless connection. The clinician conducting the assessment may communicate with the DCU 30 using a keyboard 40 and display device 50. In the alternate embodiment that utilizes a DCU 30 remote from the DAU 20, an additional keyboard and display device may be attached to the DAU 20 for the use of the clinician.

After the DCU 30 receives the sampled values from the DAU 20, the DCU 30 first examines in step 26 the sampled EEG signals for artifact arising from patient movement, eye blinks, electrical noise, etc. Detected artifact is either removed from the signal, or the portion of the signal with artifact is excluded from further processing. The EEG signal is also filtered to reduce or remove artifact from high and/or low frequency noise sources, such as electromyographic and radio frequency interference and movement artifact, respectively. Low-pass filtering is also employed prior to sampling to reduce the power at frequencies above the signal band of interest, preventing that power from appearing artifactually at lower frequencies due to an inadequate sampling frequency (aliasing).

The DCU 30 next computes a set of parameters from the artifact-free EEG data in step 28. Parameters may be derived from power spectral arrays, higher-order spectral arrays (bispectrum, trispectrum, etc.), cordance (such as described in U.S. Pat. Nos. 5,269,315 and 5,309,923), z-transformed variables, entropy metrics, and time-domain metrics, including but not limited to parameters derived from various techniques applied to the various data series, such as template matching, peak detection, threshold crossing, zero crossings and Hjorth descriptors. Such parameters, which quantify some aspect of the data, are referred to as features. Features may also be formed from combinations of parameters. An index is a function incorporating one or more features as variables. The index function may be linear or nonlinear, or may have an alternative form such as a neural network. In step 32, the DCU 30 calculates from all the parameters a series of features and indices that are predictive of the probability the subject may experience adverse events, such as suicide ideation or suicidal actions. These features and indices may be displayed to the user on the display device 50 in step 34. In the embodiment in which the DCU 30 is remote from the DAU 20, the result may be transmitted back to the display device on the DAU 20, or transmitted to the patient's physician via e-mail or made available via a secure internet World Wide Web page.

In the preferred embodiment, the EEG data is collected using Ag-AgCl electrodes of the type sold by Grass-Telefactor of Warwick, R.I. under the designation Model F-E5SHC. A bipolar 4-channel electrode montage is preferentially utilized, with each EEG channel collected as the voltage difference between each of the four pairs of electrodes F7-Fpz, F8-Fpz, A1-Fpz and A2-Fpz (International Ten-Twenty System of Electrode Placement, Jasper) where A1 is the left earlobe and A2 is the right earlobe. When the electrodes are all to be placed below the hairline, the electrodes are preferably of the Zipprep® type manufactured by Aspect Medical Systems, Inc. of Newton, Mass. or other such Ag-AgCl electrodes, such as those manufactured by Grass-Telefactor, Inc. When electrodes are placed within the hair, gold-cup type electrodes may be used, held in place by either collodion or a physical restraint such as an electrode cap placement device, as provided by various manufacturers. A variety of different electrode placements, or montages, may be used.

In the preferred embodiment, EEG signals are sampled by the A-D converter 25 at 128 samples-per-second, preferably while the subject's eyes are closed in order to minimize eye-blink artifacts. The sampled EEG signal from each electrode pair is processed independently; the initial processing will be described for a single channel, but it should be understood that it is identical for each channel. The sampled EEG signal is divided into non-overlapping, 2-second epochs. In the preferred embodiment, 4 minutes of EEG data is processed, consisting of 120 non-overlapping, consecutive, 2-second epochs. For each 2-second epoch, a power spectrum (at 0.5 Hz resolution) is calculated using a Fast Fourier Transform (FFT) after first mean de-trending to remove the DC (offset) component of the signal and then minimizing spectral leakage (smearing) by multiplying the epoch with a Hamming window. The median power spectrum of the 120 epochs is calculated by computing the median of the corresponding frequency values of the power spectra associated with each of the 120 epochs. Absolute and relative powers are calculated from the median power spectrum for a set of predefined frequency bands; these are the theta (4-7.5 Hz), alpha (8-11.5 Hz), theta+alpha (4-11.5 Hz) and total power (2-20 Hz) frequency bands. The absolute power is calculated as the sum of the power within each specific frequency band in the median power spectrum, and the relative power is calculated as the ratio of the absolute power of a specific frequency band to the absolute power of the total power frequency band. Various absolute and relative powers as well as combinations, products and ratios of absolute and relative powers within and among the EEG channels are combined to form a pool of candidate features.

It would be obvious to those skilled in the art that the pool of candidate features could be extended beyond power spectral features to include features derived from other methods of representing EEG information, including, but not limited to, bispectral analysis, time-frequency analyses, entropy metrics, fractal metrics, correlation dimension, as well as cross-channel analyses including coherence, cross-spectra, cross-bispectral features and mutual information metrics.

In the preferred embodiment, a set of EEG features are combined to form an index whose value is predictive of the probability that the subject will respond to antidepressant treatment. The mathematical structure of the index, the variables and the coefficients used and their method of combination were developed using a statistical modeling technique.

Following Institutional Review Board approval and written informed consent, 36 outpatients meeting DSM-IV (Diagnostic and Statistical Manual of Mental Disorders—Fourth Edition) criteria for Major Depressive Disorder (MDD) entered an 8-week prospective treatment trial with open-label, flexible dose selective serotonin reuptake inhibitor (SSRI) antidepressants. The 17-item Hamilton Depression Rating Scale (Ham-D) was administered at unmedicated baseline and at weeks 1, 4 and 8 during treatment to assess changes in depressive symptoms. Treatment response as defined as a reduction of the Ham-D score at week 8 of at least 50% from baseline. At each study visit (baseline, weeks 1, 4 and 8) serial, 4-channel EEGs were sampled at 128 samples-per-second, and recorded to computer using an Aspect A1000 EEG Monitor sold by Aspect Medical Systems of Newton, Mass.). As described above, a pool of candidate EEG features were extracted from each recording.

Using the binary treatment response as the dependent variable, logistic regression was used to identify those candidate EEG features measured at baseline and week 1 which were, when combined in a model, predictive of response to treatment. The resultant logistic model predicted the probability of response to treatment ("Pred2", scaled 0 to 100%):

$$Pred2 = 100 \Big/ \left(1 + e^{2.7355 \cdot \left(1 - \frac{BMRT12}{MRT12_{one\_week}}\right) + 39.0795 \cdot MRT78_{one\_week} + 14.6946 \cdot BDRTAS12 - 9.0977}\right)$$

where:

MRT12 is the mean of the relative theta powers calculated on channels A1-Fpz and A2-Fpz, MRT12$_{one\_week}$ is the value of MRT12 measured at one week, BMRT12 is the value of MRT12 measured at baseline, MRT78 is the mean of the relative theta powers calculated on channels F7-Fpz and F8-Fpz, MRT78$_{one\_week}$ is the value of MRT78 measured at one week, DRTAS12 is the value of the combined relative theta+alpha power on channel A1-Fpz minus the combined relative theta+alpha power on channel A2-Fpz (DRTAS12 is therefore a measure of left-minus-right asymmetry), DRTAS12$_{one\_week}$ is the value of DRTAS 12 measured at one week and BDRTAS12 is the value of DRTAS12 measured at baseline.

In the preferred embodiment, the structure of the index Pred2 and its components were further refined to form an index whose value is predictive of the probability of the subject suffering an adverse event. In the preferred embodiment, the adverse event is the ideation of suicide (e.g., the occurrence of suicidal thoughts or actions, as quantified by a neurocognitive assessment scale).

In order to evaluate the ability of the Pred2 Index to predict suicide ideation, following model development additional subjects were added to the database for a total of 42 subjects. Item 3 of the Hamilton Depression Rating Scale was examined for each subject to identify those individuals who developed new (or worsening) symptoms of suicide ideation. Pred2 and its components were evaluated to determine if they could predict which subjects would have new or worsening symptoms of suicide ideation. These variables were also evaluated to determine if they correlated with change in severity of symptoms of suicide ideation from baseline.

Figure 3:
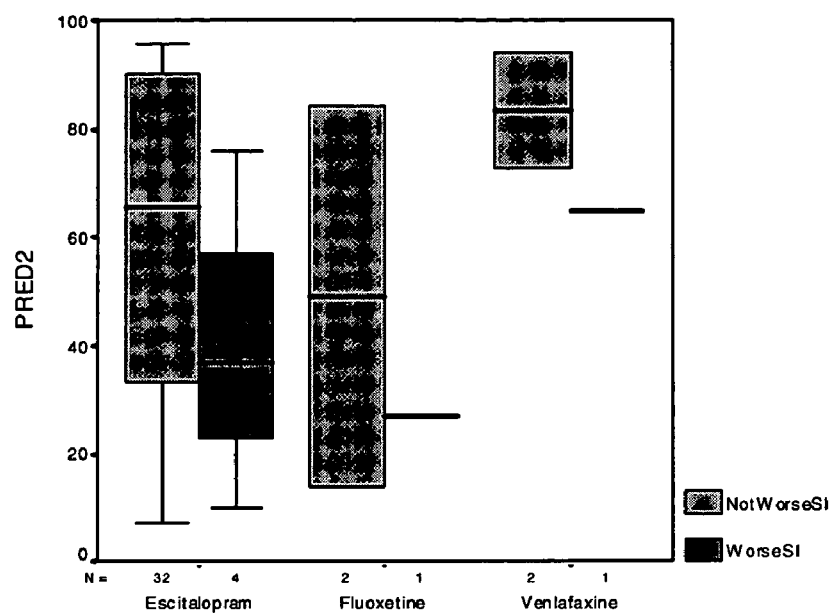
FIG. 3 is an error bar chart showing the values of the Index Pred2 for the Worsening Suicide Ideation (SI) and Not Worsening SI groups, stratified by antidepressant treatment.
Figure 4:
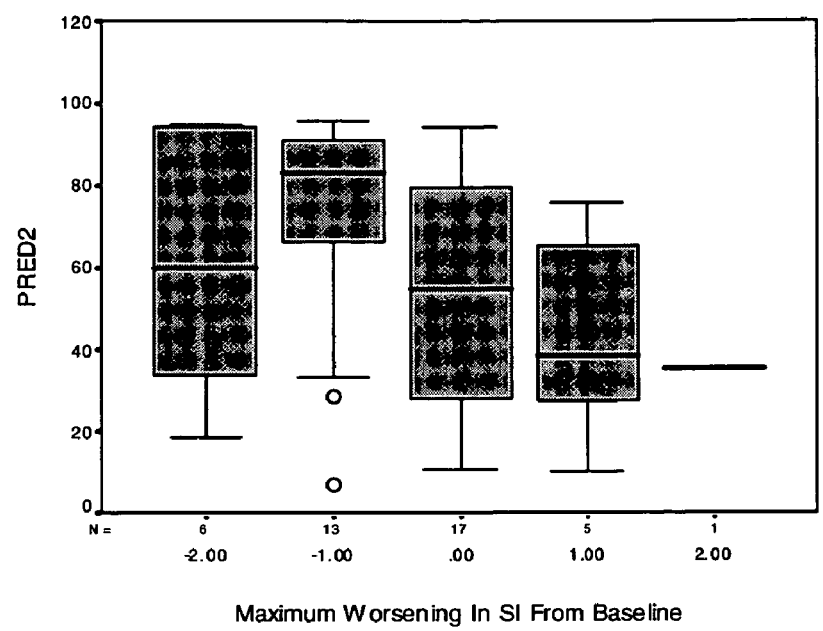
FIG. 4 is an error bar chart showing the value of Pred2 vs. the maximum change from baseline observed in Ham-D item 3 during the first four weeks of treatment.

A binary-valued variable (SuicideGroup) was calculated for each subject to indicate whether the subject developed new or worsening symptoms of suicide ideation (WorseSI) or not (NotWorseSI) at visits at 1 and 4 weeks. Analysis of variance of Pred2, controlling for the antidepressant treatment the patient later received (i.e., escitalopram, fluoxetine or venlafaxine), demonstrated that the values of Pred2 were significantly different between the WorseSI and NotWorseSI groups (p=0.005) when accounting for differences among treatment groups (FIG. 3 The horizontal line across the inside of the box is the median value of the data points in each subgroup, while the upper and lower box edges are the 75$^{th}$ and 25$^{th}$ percentiles, respectively, and thus the box length is the interquartile range. The horizontal lines at the end of the "whiskers" above and below the boxes represent the most extreme values of the data points in each subgroup). Pred2 also correlated with maximal worsening of suicide ideation (SI) within the first four weeks of treatment (Spearman rank correlation (R)=−0.307, p=0.047) as shown in FIG. 4. In addition, the baseline left-minus-right relative theta+alpha asymmetry feature (BDRTAS12) was borderline significantly different between the WorseSI and NotWorseSI groups (p=0.053). Subjects who developed new suicide ideation (SI) symptoms generally had positive (i.e., left-dominant) asymmetry. The feature BDRTAS 12 seems to perform similarly regardless of which antidepressant treatment the patient later receives (FIG. 5).

Figure 6:
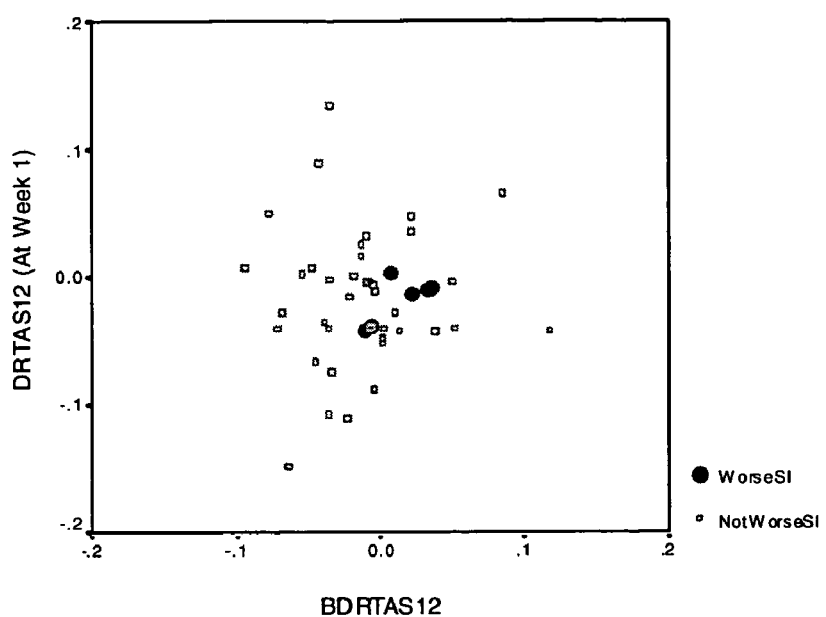
FIG. 6 is a scatter plot of left-minus-right relative theta+alpha asymmetry measured at baseline (BDRTAS12) and at 1 week (DRTAS12).

The use of baseline relative theta+alpha asymmetry (BDRTAS12) as a predictor of future development of SI symptoms achieved the following performance in this dataset: 67% sensitivity, 78% specificity and 76% accuracy, with 33% positive predictive accuracy (PPA) and 93% negative predictive accuracy (NPA). Relative theta+alpha asymmetry (DRTAS 12$_{one\_week}$) measured at week 1 provides additional information that improves discrimination of subjects who do (and don't) develop SI symptoms (FIG. 6). EEG asymmetry in subjects who developed new SI symptoms initially was >0 at baseline, and did not significantly decrease after 1 week of treatment. Using a detection rule that classifies subjects having both BDRTAS12>0 and DRTAS 12$_{one\_week}$>−0.02 as being likely to develop SI symptoms and the remaining subjects as being not likely to develop SI symptoms achieved the following performance in this dataset: 67% sensitivity, 89% specificity and 86% accuracy, with 50% PPA and 94% NPA.

Figure 5:
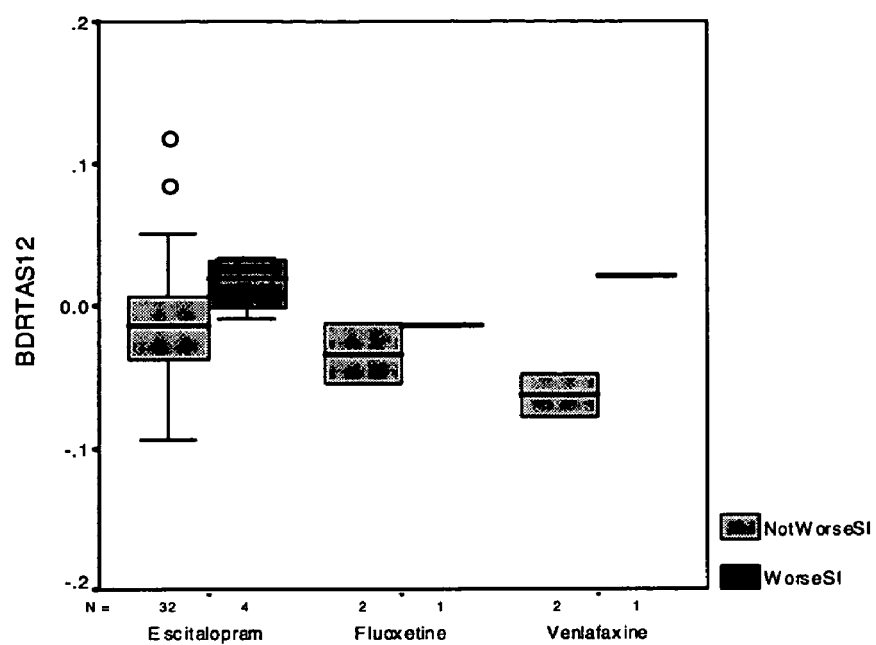
FIG. 5 is an error bar chart showing the baseline value of the left-minus-right relative theta+alpha asymmetry feature (BDRTAS12) for the Worsening SI and Not Worsening SI groups, stratified by antidepressant treatment.

FIG. 5 shows that the distance from the origin (0,0) of the DRTAS12$_{one\_week}$ vs. BDRTAS12 relationship is a predictor of the probability of suicide ideation in a specific individual. All those patients who experienced suicide ideation were tightly clustered at the center of the DRTAS12$_{one\_week}$ vs. BDRTAS12 scatter plot. Among those patients corresponding to data points far from the origin there were no instances of suicide ideation. Therefore, an alternate embodiment of the invention is derived from the sum of the absolute values of DRTAS12$_{one\_week}$ and BDRTAS12.

$$\text{Index}_{suicide\_ideation} = |DRTAS12_{one\_week}| + |BDRTAS12|$$

A very low risk of suicide ideation is associated with values of Index$_{suicide\_ideation}$>0.06. In an alternate embodiment, a mathematically intuitive measure of the risk of suicide ideation may be constructed as the distance of a data point from the origin of the scatter plot in FIG. 5, computed as $$\text{Index}_{suicide\_ideation2} = (|DRTAS12_{one\_week}|^2 + |BDRTAS12|^2)^{1/2}$$

Increasing distances from the origin, expressed as increasing values of Index$_{suicide\_ideation2}$, are predictive of a decreasing probability of suicide ideation.

The EEG Pred2 index and the EEG asymmetry features DRTAS12$_{one\_week}$ and BDRTAS12 are useful predictors of response to treatment and probability of adverse events, especially suicide ideation. Change in these metrics in response to initial treatment may provide additional information that might improve prediction performance. Although these metrics were developed to predict responses related to pharmacological treatment, it is anticipated that they may predict response to other forms of treatment, including, but not limited to, psychotherapy, electroconvulsive therapy (ECT), transmagnetic stimulation and various forms of neurostimulation including deep brain stimulation and peripheral nerve stimulation (e.g., vagus nerve stimulation).

Although the indices (metrics) of the preferred embodiment were developed to predict responses and events related to treatment of depression, it is anticipated that these metrics may predict response and/or adverse events when treating other types of psychological and neurological disorders, including, but not limited to, anxiety, bipolar depression, mania, schizophrenia, obsessive-compulsive disorder and dementia.

The above study demonstrated that the EEG Pred2 index, the EEG asymmetry features DRTAS12$_{one\_week}$ and BDRTAS12, and the indices Index$_{suicide\_ideation}$ and Index$_{suicide\_ideation2}$, may be used to predict onset of adverse symptoms, including changes in suicide ideation and suicidal actions. These indices, as well as other EEG-based indices, hereafter referred to as EEG Index, may also be used prior to treatment to predict eventual onset of symptoms due to treatment.

The EEG Index may be computed and used to predict the onset of adverse symptoms throughout the course of therapy.

The EEG Index may be used to predict other adverse symptoms such as somatic symptoms, sexual side-effects, nausea, vomiting and other symptoms not considered to be manifestations of improvement of the psychological and/or neurological condition.

While the foregoing invention has been described with reference to its preferred embodiments, various alterations and modifications will occur to these skilled in the art. All such alterations and modifications are intended to fall within the scope of the appended claims.

We claim:

1. A system for predicting a psychological and neurological adverse event from electroencephalographic (EEG) signals comprising:
   a data acquisition unit for acquiring electroencephalographic signals from a subject being evaluated,
   a processor for:
      computing at least one parameter from said electroencephalographic signals,
      deriving a first feature from said at least one parameter at a pre-treatment condition,
      deriving a second feature from said at least one parameter after an initiation of treatment of the subject,
      creating an index by combining said first feature and said second feature, and
      predicting the adverse event through the use of said index,
   wherein said treatment is pharmacological treatment, psychotherapy, electroconvulsive therapy, transmagnetic stimulation or neurostimulation and wherein said adverse event is suicidal thoughts, suicidal actions, somatic symptoms, sexual side-effects, nausea or vomiting.

2. The system for predicting a psychological and neurological adverse event from electroencephalographic signals of claim 1, wherein said index combining said first and second features is a distance from an origin to a point represented by said first and second features.

3. The system for predicting a psychological and neurological adverse event from electroencephalographic signals of claim 1 wherein said at least one parameter is computed using a combination of relative EEG theta power and relative combined theta+alpha asymmetry.

4. The system for predicting a psychological and neurological adverse event from electroencephalographic signals of claim 1, wherein said first feature and said second feature are relative theta frequency band power.

5. The system for predicting a psychological and neurological adverse event from electroencephalographic signals of claim 1, wherein said first feature and said second feature are relative theta+alpha frequency band asymmetry.

6. A method of predicting a psychological and neurological adverse event from electroencephalographic (EEG) signals, comprising the steps of:
   acquiring electroencephalographic signals from a subject being evaluated,
   computing with a processor at least one parameter from said electroencephalographic signals,
   deriving a first feature from said at least one parameter at a pre-treatment condition,
   deriving a second feature from said at least one parameter after an initiation of treatment of said subject,
   creating an index by combining said first feature and said second feature,
   predicting the psychological and neurological adverse event through the use of said index, and
   wherein said treatment is pharmacological treatment, psychotherapy, electroconvulsive therapy, transmagnetic stimulation or neurostimulation and wherein said adverse event is suicidal thoughts, suicidal actions, somatic symptoms, sexual side-effects, nausea or vomiting.

7. The method of predicting a psychological and neurological adverse event from electroencephalographic signals of claim 6, wherein said first feature and said second feature are relative theta frequency band power.

8. The method of predicting a psychological and neurological adverse event from electroencephalographic signals of claim 6, wherein said first feature and said second feature are relative theta+alpha frequency band asymmetry.

9. The method of predicting a psychological and neurological adverse event from electroencephalographic signals of claim 6, wherein said index combining said first and second features is a distance from an origin to a point represented by said first and second features.

10. The method of predicting a psychological and neurological adverse event from electroencephalographic signals of claim 6 wherein said at least one parameter is computed using a combination of relative EEG theta power and relative combined theta+alpha asymmetry.

* * * * *